Figure 1:
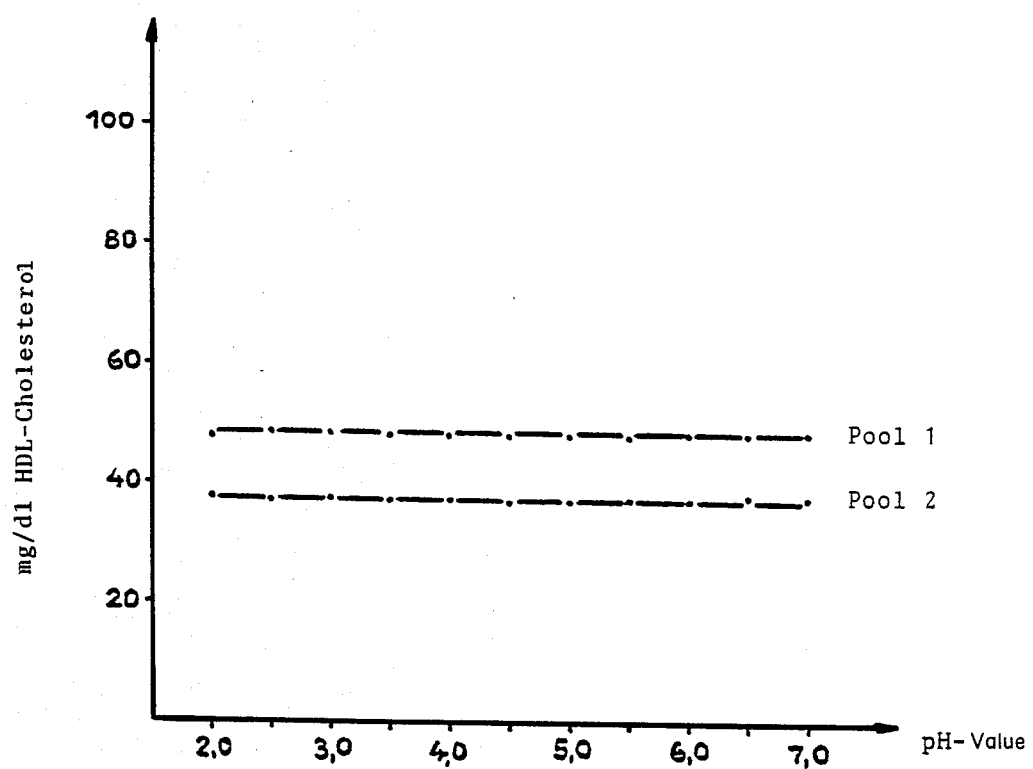

United States Patent [19]

Draeger et al.

[11] Patent Number: 4,521,519

[45] Date of Patent: Jun. 4, 1985

[54] REAGENT FOR THE PRECIPITATION OF APO-B-CONTAINING LIPOPROTEINS

[75] Inventors: Brigitte Draeger, Tutzing; Joachim Ziegenhorn, Starnberg, both of Fed. Rep. of Germany

[73] Assignee: Boehringer Mannheim GmbH, Mannheim, Fed. Rep. of Germany

[21] Appl. No.: 369,382

[22] Filed: Apr. 19, 1982

[30] Foreign Application Priority Data

May 2, 1981 [DE] Fed. Rep. of Germany ....... 3117455

[51] Int. Cl.$^3$ ............................................ G02N 33/48
[52] U.S. Cl. ..................................... 436/17; 436/174; 436/825
[58] Field of Search ................... 436/17, 13, 86, 174, 436/175, 177, 811, 815, 825

[56] References Cited

U.S. PATENT DOCUMENTS 3,873,433  3/1975  Seidel et al. ................... 204/180 G
4,210,557  7/1980  Handschuh ........................ 252/408
4,226,713  10/1980 Goldberg ......................... 23/230 B

OTHER PUBLICATIONS

Burstein, M. et al., Life Sciences, vol. 8(8), pp. 345–348, (1969).

Lopes-Virella, M. et al., Clin. Chem., vol. 23(5), pp. 882–884, (1977).

Warnick, G. R. et al., Clin. Chem., vol. 25(4), pp. 596–604, (1979).

Pinkowitz, R. A. et al., Clin. Chem., vol. 25(6), p. 1146, Abstract 416 (1979).

Hohenwaller, W. et al., Clin. Chem., vol. 26(1), pp. 177–178, (1980).

Draeger, B. et al., Lipopr. Coron. Heart Dis. Int. Symp., pp. 38–42, (1979).

Sale et al., Clinica Chimica Acta, vol. 112, pp. 375–377, (1981).

Warnick, G. R. et al., Am. J. Clin. Path., vol. 78(5), pp. 718–723, (1982).

Burstein, M. et al., Journal of Lipid Research, vol. 11, pp. 583–595, (1970).

Clin. Chem. 25 (1979), pp. 939–942, Kosner, G. M. et al.,

Draeger et al., Lipoproteine und Herzinfarkt.

*Primary Examiner*—Ben R. Padgett
*Assistant Examiner*—M. Morkowitz
*Attorney, Agent, or Firm*—Felfe & Lynch

[57] ABSTRACT

The present invention provides a reagent for the precipitation of apo-B-containing lipoproteins, wherein it comprises 0.2 to 3 grams per liter of phosphotungstic acid and more than 2 mmols per liter of magnesium ions in aqueous solution.

The present invention also provides a process for the preparation of this reagent and a process for the precipitation of apo-B-containing lipoproteins using this reagent.

27 Claims, 2 Drawing Figures

REAGENT FOR THE PRECIPITATION OF APO-B-CONTAINING LIPOPROTEINS

The present invention is concerned with a reagent for the precipitation of apo-B-containing lipoproteins and with a process for the preparation of this reagent and is also concerned with the use of the reagent for the determination of HDL cholesterol.

High density lipoproteins (HDL) have achieved considerable interest in recent years. It has been shown that there is an inverse relationship between HDL cholesterol and the risk of heart infarct. If the proportion of HDL cholesterol in the blood is low, then there is an increased risk of heart infarct. The possibility of determining HDL cholesterol is an important component for the assessment of the individual risk of atherosclerosis since, from a knowledge of the HDL cholesterol value, it is not only possible to make a prediction regarding this protective lipoprotein fraction but also to draw conclusions with regard to the amount of the strongly atherogenic LDL cholesterol by way of the known approximation formula:

LDL cholesterol = total cholesterol −
1/5 total glycerides − HDL cholesterol

The usual prerequisite for the determination of the cholesterol content of the HDL fraction is a separation of all other classes of lipoproteins, to which belong chylomicrons, very low density lipoproteins (VLDL) and low density lipoproteins (LDL), these belonging to the apo-B-containing lipoprotein class.

For the separation of these apo-B-containing lipoproteins, there are, in particular, used ultra-centrifuging, electrophoresis and precipitation methods. Of these three methods, the precipitation methods, in which usually a mixture of a polyanion and a divalent cation is used, are the most practicable to carry out. Besides precipitation with heparin-manganese ions or with dextran sulfate-magnesium ions, use is very frequently made of a precipitation with phosphotungstate-magnesium ions, this latter method being described, for example, in Journal of Lipid Research, 11, 583–595/1970.

For carrying out this method, a phosphotungstate solution is adjusted to a particular pH value with aqueous sodium hydroxide solution, preferably to pH 6.1 to 7.6. The phosphotungstate solution thus obtained is added to the sample to be measured, for example to serum or plasma, and, in addition, a magnesium chloride solution is added. The following amount ratios are conventional:

1.000 ml. sample
0.100 ml. phosphotungstic acid solution (40 g./l., pH 6.1–7.6)
0.025 mol magnesium chloride hexahydrate solution (2 mol/l.)

In this way, the apo-B-containing lipoproteins are precipitated out and separated off by centrifuging. HDL cholesterol and other HDL parameters, for example apolipoproteins and phospholipids, can then be determined in the precipitation supernatant.

The addition of phosphotungstate and magnesium chloride solution to the sample can also take place in the form of a mixture (cf. Clin. Chem., 25, 939–942/1979; and Lipoproteine und Herzinfarkt, pub. H. Greten, P. D. Lang and G. Schettler, Verlag Gerhard Witzrock Baden-Baden, Köln, New York, pp. 39–44/1979). This procedure increases the practicability of the carrying out of the test. According to this variant, 1.0 ml. of sample is mixed with 0.1 ml. of the phosphotungstate-magnesium chloride solution mixture. However, in contradistinction to the individual solutions, the mixture of phosphotungstate and magnesium chloride solution is not stable for a long time since precipitates from in the precipitation reagent.

Furthermore, a great disadvantage of the previously described precipitation methods is that, in the case of triglyceride-rich samples, after centrifuging the precipitates partially float. High g values and long centrifuging times are necessary in order to obtain clear precipitation supernatants.

A further disadvantage of the known precipitation method with phosphotungstate/magnesium ions is that the precipitation shows a dependency upon the pH value. It is recommended to carry out the precipitation at a pH value of the phosphotungstate solution of 6.1 to 7.4. However, the adjustment of a definite pH value gives rise to considerable difficulties since the phosphotungstic acid in the concentrations ranges previously used for the precipitation influences the glass electrode used for the pH measurement.

In addition, it is disadvantageous in the previous precipitation methods that, in the case of the small volumes of reagent to be added, conventional dilutors, which would make possible an exact measurement of the reagent volume, cannot be used. A prerequisite for the use of a diluent is generally a ratio of at least 2 parts by volume of precipitation reagent per 1 part by volume of sample.

It is an object of the present invention to provide a new reagent for the precipitation of apo-B-containing lipoproteins which no longer displays the above-mentioned disadvantages and can be used for a precise, readily carried out precipitation and centrifuging of the apo-B-containing lipoproteins so that a problem- and disturbance-free HDL cholesterol determination in the centrifuge supernatant is possible.

Thus, according to the present invention, there is provided a reagent for the precipitation of apo-B-containing lipoproteins, which contains 0.2 to 3 g./liter and preferably 0.25 to 2 g./liter of phosphotungstic acid and more than 2 mmol/l. and preferably 4 to 25 mmol/liter of magnesium ions in an appropriate solvent.

The magnesium ions can be added to the reagent in the form of an appropriate magnesium salt and preferably as magnesium chloride hexahydrate. Water is particularly preferred as the solvent.

An important advantage of the reagent according to the present invention is that the HDL cholesterol values found after precipitation of the apo-B-containing lipoproteins do not display a pH dependency (see FIG. 1 of the accompanying drawings). Consequently, it is no longer necessary to adjust the precipitation reagent to a definite and preferably neutral pH value as in the case of the prior art. Therefore, the precipitation reagent according to the present invention is especially advantageously used with a pH value such as is obtained upon dissolving the phosphotungstic acid and the magnesium salt in the solvent used. This pH value is, for example, in the case of using magnesium chloride hexahydrate or magnesium sulphate 2.2 to 2.7 and in the case of using magnesium acetate 5.4 to 5.7.

As is shown by FIG. 1 of the accompanying drawings, with a precipitation reagent according to the present invention, a complete precipitation of apo-B-containing lipoproteins can also be achieved even when the pH value of the precipitation reagent mixture is adjusted to higher values. This can take place by the addition of the necessary amount of an appropriate base, for example an aqueous sodium hydroxide solution. However, pH values above about 8.0 in the precipitation agent mixture are limiting since, in the case of such pH values, the magnesium ions precipitate out in the form of magnesium hydroxide. Thus, the pH value of the precipitation agent is preferably 2 to 8.

Surprisingly, we have found that, in contradistinction to the known precipitation reagent mixtures of phosphotungstate and magnesium salts, the precipitation reagent according to the present invention displays an excellent stability. After storage for 12 months at 50° C., the reagent is still fully capable of functioning. No formation of precipitate occurs in the reagent.

Furthermore, we have, surprisingly, found that with the precipitation reagent mixture according to the present invention, the lipoprotein-containing precipitate can be centrifuged without any problems. For the complete separation of the precipitate, a period of centrifuging of 5 to 10 minutes at 1500 g generally suffices. This advantage manifests itself especially in the case of centrifuging the precipitates from samples with a high lipid content.

In the following Table 1, the HDL cholesterol values, measured after precipitation of apo-B-containing lipoproteins, are compared, on the one hand, with the use of a known precipitation reagent (sample:reagent 1.0:0.1) and, on the other hand, with the use of the precipitation reagent according to the present invention (sample:reagent 1.0:2.0) for such lipaemic serum samples.

TABLE 1

HDL-cholesterol values of lipaemic samples (high proportion of triglycerides), measured after precipitation and subsequent centrifuging of apo-B-containing lipoproteins:
A with known precipitation reagent (sample:reagent 1.0:0.1) (phosphotungstate: 40 g./l., adjusted to pH 6.1–7.6 with aqueous sodium hydroxide solution; $MgCl_2.6H_2O$: 0.500 mol/l.)
B with precipitation agent of the invention (sample:reagent 1.0:2.0) (1.84 g./l. phosphotungstic acid; 0.025 mol/l. $MgCl_2.6H_2O$)

| Serum | content of total cholesterol [mg/dl] | triglycerides [mg/dl] | HDL-cholesterol precipitation method A [mg/dl] | B [mg/dl] |
|---|---|---|---|---|
| 1 | 170 | 460 | 19.5 | 19.3 |
| 2 | 181 | 467 | 27.5 | 26.8 |
| 3 | 215 | 440 | 41.3 | 41.1 |
| 4 | 197 | 710 | floats, turbid | 25.7 |
| 5 | 494 | 522 | 17.7 | 18.1 |
| 6 | 270 | 928 | turbid | 18.1 |
| 7 | 298 | 464 | 21.0 | 23.2 |
| 8 | 257 | 696 | floats, turbid | 28.7 |
| 9 | 323 | 1348 | floats | floats |
| 10 | 291 | 1078 | floats | 37.4 |
| 11 | 695 | 1566 | floats | turbid |
| 12 | 250 | 522 | floats, turbid | 30.8 |
| 13 | 273 | 1174 | floats | 36.2 |
| 14 | 310 | 652 | floats | 30.2 |
| 15 | 261 | 1073 | floats | 12.4 |
| 16 | 178 | 681 | floats | 20.5 |
| 17 | 221 | 1044 | floats, turbid | turbid |
| 18 | 348 | 942 | floats | slightly turbid |
| 19 | 216 | 957 | floats, turbid | turbid |
| 20 | 262 | 701 | floats, turbid | 16.5 |
| 21 | 308 | 464 | floats, turbid | 32.7 |
| 22 |  | 796 | turbid | 26.5 |

TABLE 1-continued

HDL-cholesterol values of lipaemic samples (high proportion of triglycerides), measured after precipitation and subsequent centrifuging of apo-B-containing lipoproteins:
A with known precipitation reagent (sample:reagent 1.0:0.1) (phosphotungstate: 40 g./l., adjusted to pH 6.1–7.6 with aqueous sodium hydroxide solution; $MgCl_2.6H_2O$: 0.500 mol/l.)
B with precipitation agent of the invention (sample:reagent 1.0:2.0) (1.84 g./l. phosphotungstic acid; 0.025 mol/l. $MgCl_2.6H_2O$)

| Serum | content of total cholesterol [mg/dl] | triglycerides [mg/dl] | HDL-cholesterol precipitation method A [mg/dl] | B [mg/dl] |
|---|---|---|---|---|
| 23 |  | 833 | floats | 28.5 |

The values summarised in Table 1 show that difficulties in the case of precipitating apo-B-containing lipoproteins or in the case of centrifuging off the precipitates with the precipitation reagent according to the present invention only occur in the case of substantially higher lipid (triglyceride) contents than with the known precipitation reagent. This leads to a further advantage in comparison with the previously known phosphotungstate/magnesium salt precipitation: a predilution of the lipaemic samples before the addition of the precipitation reagent is only necessary in the case of very high triglyceride values (above 1000 mg./dl.). In the case of the previously described precipitation variants, a predilution of the sample to be determined was necessary even in the case of triglyceride values of about 400 mg./dl.

The present invention also provides a process for the preparation of the reagent according to the present invention. According to this process, the phosphotungstic acid, together with the magnesium salt, is dissolved in an appropriate solvent and preferably in water. A solution is obtained, the pH value of which is substantially dependent upon the magnesium salt used. The solution thus obtained can then be used according to the present invention. A different pH value can, if desired, be adjusted by the addition of aqueous sodium hydroxide solution. It is advantageous to dissolve the phosphotungstic acid and the magnesium salt separately in the solvent and subsequently to mix together the solutions obtained.

The present invention also provides a process for the precipitation of apo-B-containing lipoproteins from body fluids, wherein the precipitation reagent according to the present invention is added to the sample to be determined.

Since the precipitation reagent according to the present invention contains the phosphotungstic acid and the magnesium ions in substantially lower concentrations than the known precipitation reagents, the former can be added in a substantially greater volume to the sample than is the case with the previously known precipitation methods with phosphotungstate/magnesium ions. This provides the advantage that in the case of the precipitation method according to the present invention, dilutors can readily be used. As is known, the use of dilutors provides considerable advantages, especially with regard to the practicability of carrying out the test, for example a great saving of time, improved precision, smaller consumption of materials and the like. A manual measurement of sample and precipitation reagent does not take place so that the possibilities of error are decisively reduced. The volumes can be determined more accurately. The precision of the precipitation of the apo-B-containing lipoproteins and thus of the subsequent HDL-cholesterol determination is thereby decisively improved. The greater is the proportion by volume of the precipitation reagent in the total volume of the precipitation batch, the smaller are the entrainment problems from one batch to another in the case of automation of the HDL-cholesterol determination by the use of dilutors.

A limiting factor for the proportion by volume of the precipitation reagent in the total volume is the sensitivity of the methods which are available for the subsequent determination of the HDL parameter to be measured in the centrifuged supernatant. The best suited sample-reagent ratio for a particular individual case can be easily determined by a few preliminary experiments. A sample-reagent ratio of 1:2 to 1:20 has proved to be advantageous for the previously known methods for the determination of the HDL parameter.

The optimum concentrations of the components of the precipitation reagent can also be easily determined by means of a few preliminary experiments. We have found that in the case of a sample:reagent ratio of 1:2, a precipitation reagent is especially suitable which contains 1.8 to 1.9 and preferably 1.84 g./liter of phosphotungstic acid and 25 mmol/liter of magnesium ions. If, to 1 part by volume of sample, there are added 2.5 parts by volume of reagent, then 1.4 to 1.5 g./liter and preferably 1.47 g./liter of phosphotungstic acid and 20 mmol/liter of magnesium ions are especially preferred. If the ratio of sample:reagent amounts to 1:20, then there is advantageously used a precipitation reagent with 0.25 to 0.35 g./liter and preferably 0.306 g./liter of phosphotungstic acid and 4.16 mmol/liter of magnesium ions.

It is known that some of the serum and plasma samples, as a result of their high triglyceride content, do not give clear precipitation supernatants or their precipitates float after centrifuging. In order to overcome these disadvantages, such samples must be prediluted. It is known that such prediluted samples, after precipitation of the apo-B-containing lipoproteins, give too low values for the HDL-cholesterol. A partial co-precipitation of the HDL takes place when precipitating out the apo-B-containing lipoproteins. In the case of the use of the precipitation reagent according to the present invention, as already mentioned above, a predilution of the sample is only necessary in the case of higher triglyceride contents than in the case of using the previously known precipitation methods. The co-precipitation of HDL, which has also been ascertained in the case of these prediluted samples, can be prevented by adding an appropriate detergent to the precipitation reagent or to the predeluent for the sample (water or physiological solution of sodium chloride). According to the present invention, non-ionic and anionic detergents are especially preferred. The non-ionic detergents are preferably polyoxyethylene-lauryl ethers, alkyl aryl ethers, polyoxyethylated octylphenol and hydroxypolyethoxydodecanes and the anionic detergents can be detergents of the sulphosuccinamate or sulphosuccinamate types, for example tetrasodium N-(1,2-dicarboxyethyl)-N-octadecylsulphosuccinamate, disodium N-octadecylsulphosuccinamate, sodium dioctylsulphosuccinate and disodium dodecylsulphosuccinate.

If the detergent is added to the precipitation reagent, then concentrations of 0.03 to 0.1% in the case of non-ionic detergents and of 0.1 to 0.3% in the case of anionic detergents have proved to be especially useful. If the detergent is added to the diluent, then the concentrations of the detergent in the diluent amount, in the case of non-ionic detergents, to 0.1 to 0.5% and in the case of anionic detergents to 0.3 to 1%.

The following Examples are given for the purpose of illustrating the present invention:

EXAMPLE 1

1. Preparation of the precipitation reagent 1.84 g. Phosphotungstic acid is dissolved ad 500 ml. with distilled water. 5.08 g. Magnesium chloride hexahydrate are dissolved ad 500 ml. with distilled water. The two solutions are mixed together. The reagent is then ready for use.

2. Precipitation of apo-B-containing lipoproteins 0.5 ml. of sample is mixed with 1 ml. of the precipitation reagent. After centrifuging for 5 to 10 minutes at 1500 g, all the apo-B-containing lipoproteins have settled out as a precipitate on the bottom of the centrifuging vessel. The clear precipitation supernatant contains HDL. In the precipitation supernatant, there can be determined, for example, HDL cholesterol with an enzymatic cholesterol test.

3. HDL-Cholesterol determination 0.2 ml. of the precipitation supernatant is mixed with 2 ml. of a reagent solution for cholesterol determination, which consists of the following components: 0.2 molar phosphate buffer (pH 7.8); 1 mmol/liter 4-aminophenazone; 5 mmol/liter phenol; 5 mmol/liter 3,4-dichlorophenol; 0.48% fatty alcohol polyglycol ether; 0.1 U/ml. cholesterol esterase; 0.14 U/ml. cholesterol oxidase; and 0.12 U/ml. peroxidase. After incubating for 20 minutes at ambient temperature, the extinction of the sample is measured in the usual way at 546 nm against the reagent blank.

The calculation takes place via the factor:

$$\text{mg./dl. } HDL\text{-cholesterol} = 302.2 \cdot \Delta E \text{ sample.}$$

Figure 2:
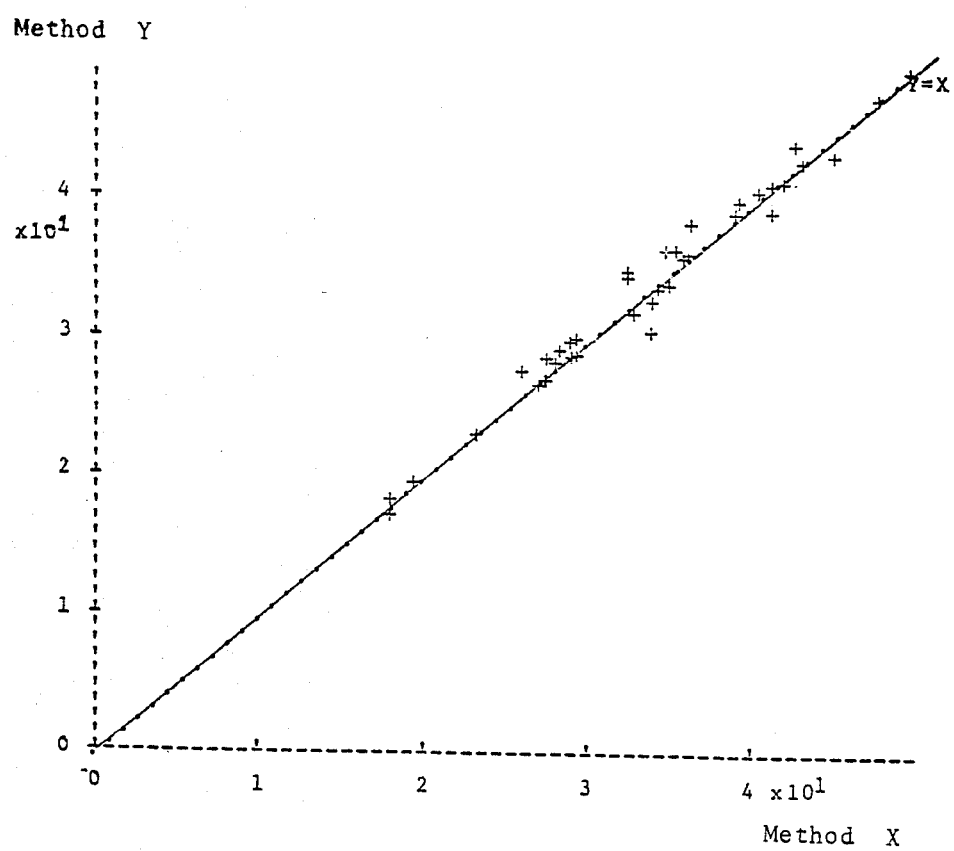

In FIG. 2 of the accompanying drawings, the values which have been obtained according to the here-described method with a ratio of sample:precipitation reagent according to the present invention of 1.0:2.0 ($\bar{Y}=33.4$ mg./dl.) are plotted against the corresponding values which have been obtained with the previously-described precipitation method with a ratio of sample: known precipitation reagent of 1.0:0.1 ($\bar{X}=33.5$ mg./dl.). As can be seen from FIG. 2, the values obtained with the two methods agree well with one another.

EXAMPLE 2

Precipitation of apo-B-containing lipoproteins in the case of a sample/precipitation reagent ratio of 1:2.5

The precipitation reagent described in Example 1 (1) is diluted with water in the ratio of 4+1. The reagent thus prepared contains 1.47 g./liter of phosphotungstic acid and 20 mmol/liter of magnesium chloride hexahydrate.

0.2 ml. of sample (serum or plasma) is mixed with 0.5 ml. of the prediluted precipitation reagent. After centrifuging for 5 to 10 minutes at 1500 g, a clear precipitation supernatant is obtained which can be used according to Example 3 for a cholesterol determination in the cholesterol test.

The HDL-cholesterol values obtained in the heredescribed manner also agree well with the values obtained according to the known methods.

EXAMPLE 3

Precipitation of apo-B-containing lipoproteins in the case of a sample/precipitation reagent ratio of 1/20 and subsequent HDL-cholesterol determination with a cholesterol test of greater sensitivity The precipitation reagent described in Example 1 (1) is diluted with water in the ratio of 1+5. A reagent is obtained containing 0.306 g./liter of phosphotungstic acid and 4.16 mmol/liter of magnesium chloride hexahydrate.

0.05 ml. of sample (serum or plasma) is mixed with 1 ml. of the diluted precipitation reagent and centrifuged for 5 to 10 minutes at 1500 g.

0.2 ml. of the clear precipitation supernatant is mixed with 2 ml. of the following reagent solution: 0.4 mol/liter of phosphate buffer (pH=7.7); 2.5 mmol 2,4-dichlorophenolsulphonic acid; 1 mmol/liter of 4-aminophenazone; 1.85 mol/liter of methanol; 0.2% hydroxypolyethoxydodecane; 0.2 U/ml. cholesterol esterase; 0.1 U/ml. cholesterol oxidase; and 0.1 U/ml. peroxidase. After incubation for 15 minutes at ambient temperature, the extinction of the sample is measured at 546 nm against the reagent blank. Evaluation takes place via a 50 mg./dl. cholesterol standard, which was treated in the same manner as the sample.

In the following Table 2, the values for HDL-cholesterol found for different serum samples in the manner here described are compared with the values which were obtained after precipitation with a sample:reagent ratio of 1:2 (see Example 1).

TABLE 2

HDL-cholesterol values for various serum samples after precipitation of apo-B-containing lipoproteins with differing ratio of sample:precipitation reagent according to the present invention.

| serum | precipitation of HDL-cholesterol with a sample:reagent ratio of | |
|---|---|---|
| | 1:2 [mg/dl] | 1:20 [mg/dl] |
| 1 | 35.2 | 35.2 |
| 2 | 53.4 | 52.8 |
| 3 | 33.9 | 33.2 |
| 4 | 65.8 | 66.9 |
| 5 | 30.0 | 29.3 |

EXAMPLE 4

Precipitation of apo-B-containing lipoproteins with detergent-containing precipitation reagent 100 ml. of the precipitation reagent described in Example 1 (1) are mixed with 0.5 ml. of a 30% aqueous solution of tetrasodium N-(1,2-dicarboxyethyl)-N-octadecylsulphosuccinamate.

0.5 of a sample diluted 1:1 with water is mixed with the detergent-containing precipitation reagent. After centrifuging for 5 to 10 minutes at 1500 g, there is obtained a clear precipitation supernatant in which the HDL-cholesterol can be determined.

In the following Table 3, the HDL-cholesterol values are summarised which have been obtained with the diluted and undiluted samples, once with and once without the addition of detergent to the precipitation agent.

TABLE 3

HDL-Cholesterol values for a diluted and undiluted sample with and without the addition of detergent to the precipitation agent.

| | HDL-cholesterol | |
|---|---|---|
| | sample undiluted [mg/dl] | sample diluted 1:1 [mg/dl] |
| precipitation with detergent-free precipitation agent | 46.1 | 42.5 |
| precipitation with detergent-containing precipitation agent (Example) | 46.3 | 46.0 |

The measurement values set out in Table 3 show that without the addition of detergent to the diluted samples, too low HDL cholesterol values are found and that the addition of a detergent is able to overcome these errors.

Similar results are also obtained when, in the above Examples, instead of tetrasodium N-(1,2-dicarboxyethyl)-N-octadecylsulphosuccinamate, other non-ionic or anionic detergents are added, for example hydroxypolyethoxydodecane (Thesit), polyoxyethylenelauryl ether (Brij 35) or polyoxyethylenealkylaryl ether (Triton-X-100) (cf. Table 4). In these cases, because of the low solubility of these detergents in the low pH range of the precipitation reagent, its pH value is increased to 5.0, preferably by the addition of aqueous sodium hydroxide solution.

TABLE 4

HDL-Cholesterol values for diluted and undiluted serum samples without and with the addition of various detergents.

| | HDL-cholesterol precipitation reagent | | | | |
|---|---|---|---|---|---|
| | without detergent addition | | with detergent addition | | |
| | | | Brij 35 | Thesit | Triton-X-100 |
| serum | sample undiluted [mg/dl] | sample diluted 1:1 [mg/dl] | 0.06% | 0.04% | 0.07% |
| | | | sample diluted 1:1 | | |
| | | | [mg/dl] | [mg/dl] | [mg/dl] |
| 1 | 45.1 | 42.5 | 45.8 | 47.5 | 46.9 |
| 2 | 45.8 | 40.8 | 46.4 | 46.4 | 46.2 |
| 3 | 34.4 | 31.8 | 33.5 | 34.1 | 34.5 |

EXAMPLE 5

Precipitation of apo-B-containing lipoproteins after dilution of the sample with detergent-containing diluent 100 ml. of water are mixed with 1.25 ml. of a 30% solution of tetrasodium N-(1,2-dicarboxyethyl)-N-octadecylsulphosuccinamate.

0.5 ml. of sample (serum or plasma) are mixed with 0.5 ml. of the detergent-containing water. To 0.5 ml. of this mixture is added 1 ml. of the detergent-free precipitation reagent described in Example 1 (1). After centrifuging for 5 to 10 minutes at 1500 g, there is obtained a clear precipitation supernatant.

In the following Table 5, there are summarised the HDL-cholesterol values found for undiluted serum samples, serum samples only diluted with water and serum samples diluted with detergent-containing water.

TABLE 5

| serum | HDL-cholesterol | | |
|---|---|---|---|
| | undiluted [mg/dl] | diluted 1:1 with water [mg/dl] | diluted 1:1 with detergent-containing water [mg/dl] |
| 1 | 40.5 | 30.7 | 41.9 |
| 2 | 53.6 | 43.0 | 55.3 |

The measurement data found show that the too low HDL-cholesterol values in the case of prediluted samples can also be avoided when a non-ionic or anionic detergent has already been added to the diluent.

In the accompanying drawings, in more detail there is shown:

FIG. 1 dependency of the HDL-cholesterol values upon the pH value after precipitation of the apo-B-containing lipoproteins with 1.84 g./liter of phosphotungstic acid and 25 mmol/liter magnesium chloride hexahydrate (sample:reagent=1.0:2.0)

FIG. 2 comparison of the HDL-cholesterol values which have been obtained after precipitation of apo-B-containing lipoproteins with a sample:precipitation reagent according to the invention ratio of 1.0:2.0 (precipitation version 1.0:2.0; Method Y) and with a sample:-known precipitation reagent ratio of 1.0:0.1 (precipitation version 1.0:0.1; Method X).

It will be understood that the specification and examples are illustrative but not limitative of the present invention and that other embodiments within the spirit and scope of the invention will suggest themselves to those skilled in the art.

What is claimed is:

1. Reagent for the precipitation of apo-B-containing lipoproteins, comprising 0.2 to 3 grams of phosphotungstic acid per liter and at least 2 mmols of magnesium ions per liter in aqueous solution.

2. Reagent as claimed in claim 1, comprising 0.25 to 2 grams of phosphotungstic acid per liter.

3. Reagent as claimed in claim 1, comprising 4 to 25 mmols of magnesium ions per liter.

4. Reagent as claimed in claim 1, comprising 0.25 to 2 grams of phosphotungstic acid per liter and 4 to 25 mmols of magnesium ions per liter.

5. Reagent as claimed in claim 1, having a pH value from 2 to 8.

6. Reagent as claimed in claim 5, wherein the pH is adjusted to 2 to 8 by the addition of sodium hydroxide.

7. Reagent as claimed in claim 1, further comprising a non-ionic detergent.

8. Reagent as claimed in claim 1, further comprising an anionic detergent.

9. Reagent as claimed in claim 7, wherein the non-ionic detergent is a polyoxyethylenelauryl ether, polyoxyethylenealkylaryl ether, polyoxyethylated octylphenol or hydroxypolyethoxydodecane.

10. Reagent as claimed in claim 8, wherein the anionic detergent is tetrasodium N-(1,2-dicarboxyethyl)-N-octadecylsulphosuccinamate, disodium N-octadecylsulphosuccinamate, sodium dioctylsulphosuccinate or disodium dodecylsulphosuccinate.

11. Reagent as claimed in claim 7, wherein the detergent is present in a concentration of from 0.03 to 0.3%.

12. Reagent as claimed in claim 8, wherein the detergent is present in a concentration of from 0.03 to 0.3%.

13. Process for the preparation of the reagent claimed in claim 1 which process comprises dissolving phosphotungstic acid and a water soluble magnesium salt in water and adjusting to a pH value of 2 to 8.

14. Process as claimed in claim 13, wherein the pH value is adjusted to a value of 2 to 8 by the addition of a base.

15. Process as claimed in claim 13, wherein the phosphotungstic acid and the magnesium salt are separately dissolved in water and the two solutions subsequently mixed together.

16. Process as claimed in claim 13, wherein 0.25 to 2 grams per liter of phosphotungstic acid and 4 to 25 mmols per liter of magnesium ions are dissolved.

17. Process for the precipitation of apo-B-containing lipoproteins which process comprises adding to the sample to measured, the reagent of claim 1, mixing the sample and reagent and allowing the precipitate to form.

18. Process as claimed in claim 17, wherein a diluent is first added to the sample to be measured, followed by adding said reagent.

19. Process as claimed in claim 17, wherein 1 part by volume of sample is mixed with 2 to 20 parts by volume of said reagent.

20. Process as claimed in claim 17, wherein 1 part by volume of sample is mixed with 2 parts by volume of said reagent which contains 1.8 to 1.9 grams per liter of phosphotungstic acid and 25 mmols per liter of magnesium ions.

21. Process as claimed in claim 17, wherein 1 part by volume of sample is mixed with 2.5 parts by volume of said reagent which contains 1.4 to 1.5 grams per liter of phosphotungstic acid and 20 mmols per liter of magnesium ions.

22. Process as claimed in claim 17, wherein 1 part by volume of sample is mixed with 20 parts by volume of said reagent which contains 0.25 to 0.35 grams per liter of phosphotungstic acid.

23. Process as claimed in claim 18, wherein a non-ionic or anionic detergent is admixed with the diluent.

24. Process as claimed in claim 23, wherein the non-ionic detergent used in a polyoxyethylenelauryl ether, polyoxyethylenealkylaryl ether, polyoxyethylated octylphenol or hydroxypolyethoxydodecane and the anionic detergent used is tetrasodium N-(1,2-dicarboxyethyl)-N-octadecylsulphosuccinamate, disodium N-octadecylsulphosuccinamate, sodium dioctylsulphosuccinate or disodium dodecylsulphosuccinate.

25. Process as claimed in claim 23, wherein the detergent is present in a concentration of 0.1 to 1%.

26. Method for the determination of HDL cholesterol, which method comprises first precipitating out of the sample to be measured, the apo-B-containing lipoproteins, centrifuging off the resultant precipitate, determining the HDL cholesterol in the supernatant and wherein for the precipitation of the apo-B-containing lipoproteins there is added the reagent of claim 1.

27. Process as claimed in claim 17, wherein the reagent contains additionally a non-ionic or anionic detergent.

* * * * *

UNITED STATES PATENT AND TRADEMARK OFFICE
CERTIFICATE OF CORRECTION

PATENT NO. : 4,521,519
DATED : June 4, 1985
INVENTOR(S) : Brigitte Draeger, et al.

It is certified that error appears in the above-identified patent and that said Letters Patent is hereby corrected as shown below:

Claim 17, line 3, after "to" insert -- be --.

Claim 24, line 2, change "in" to -- is --.

Signed and Sealed this

Seventeenth Day of December 1985

[SEAL]

Attest:

DONALD J. QUIGG

Attesting Officer     Commissioner of Patents and Trademarks